United States Patent [19]

Kato et al.

[11] Patent Number: 4,983,271
[45] Date of Patent: Jan. 8, 1991

[54] OXYGEN SENSOR

[75] Inventors: Nobuhide Kato, Ama; Masanori Katsu, Nagoya City, both of Japan

[73] Assignee: NGK Insulators, Ltd., Aichi, Japan

[21] Appl. No.: 518,437

[22] Filed: May 2, 1990

[30] Foreign Application Priority Data

May 15, 1989 [JP] Japan ............................. 1-55574[U]

[51] Int. Cl.$^5$ ........................................... G01N 27/409
[52] U.S. Cl. .................................... 204/426; 338/34; 439/676; 439/686; 439/691; 439/839; 439/913
[58] Field of Search ............... 204/425, 426, 427, 428, 204/429, 153.18; 439/913, 839, 676, 686, 691; 338/34

[56] References Cited

U.S. PATENT DOCUMENTS 4,193,965  3/1980  Cullingford et al. ........... 204/426 X
4,880,519  11/1989 Wang et al. .......................... 204/425

Primary Examiner—G. L. Kaplan
Attorney, Agent, or Firm—Parkhurst, Wendel & Rossi

[57] ABSTRACT

Excellent electrical connection between a female contact and an electrode terminal of an oxygen sensor can be assured for a long period of use even when the oxygen sensor is exposed to vibrations and/or humid atmosphere, by providing an oxygen sensor, comprising electrodes, a sensor element which generates an electromotive force or which changes its electric resistance value between the electrodes depending on oxygen concentration of a gas to be measured, electrode terminals arranged on the sensor element and connected to the electrodes, and a metallic accommodating member accommodating the sensor element, comprising; a female contact electrically connected to the electrode terminal; a ceramic housing electrically insulating the female contact from the metallic accommodating member; a resilient member pressing the ceramic housing; and a caulking ring pressing the resilient member to exhibit its resilient power; the female contact, the ceramic housing, the resilient member and the caulking ring forming a consent device receiving the electrode terminal; the caulking ring being caulked to press the resilient member such that the female contact is pressed and electrically connected to the electrode terminal by a given pressure.

2 Claims, 3 Drawing Sheets

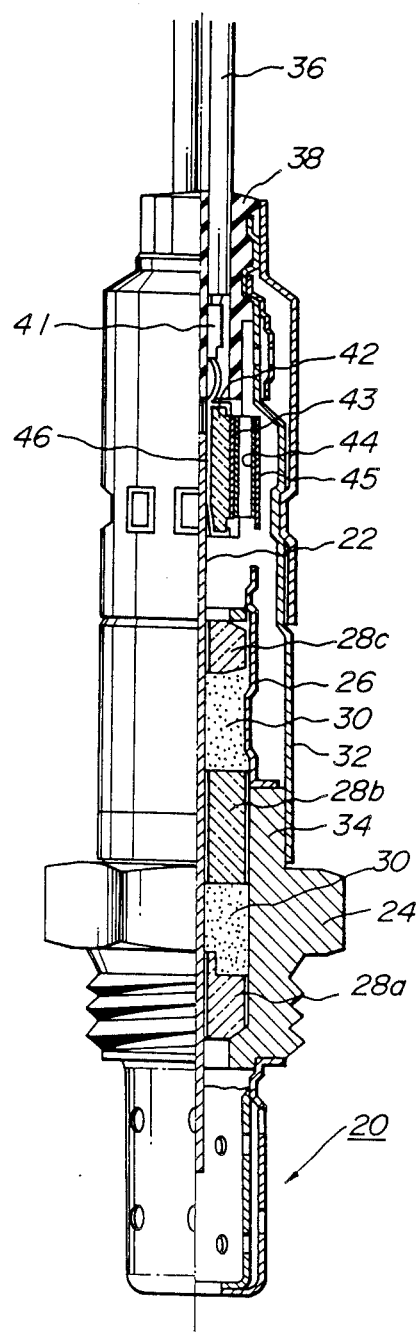
FIG_1a

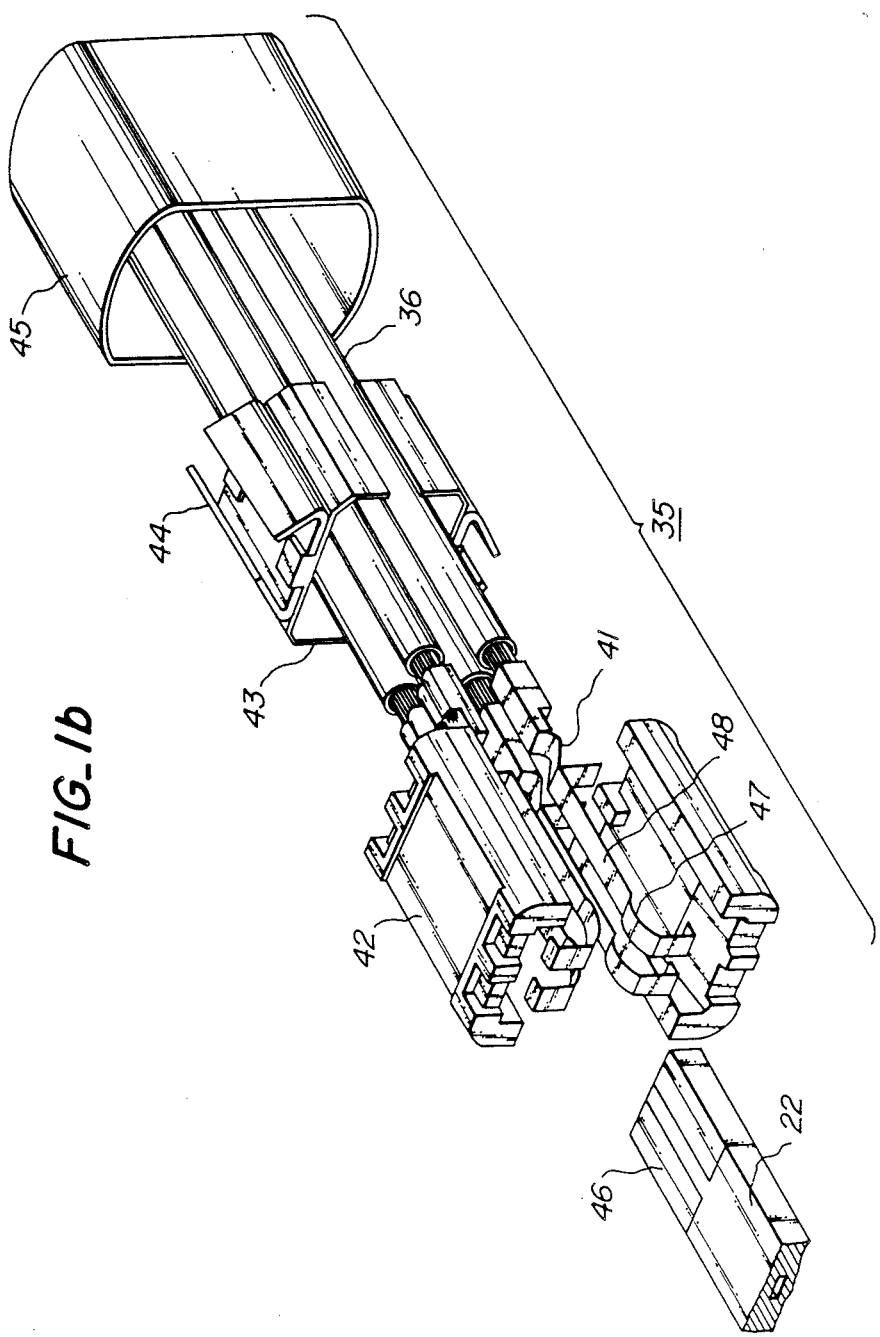
FIG_1b

FIG_2a
PRIOR ART
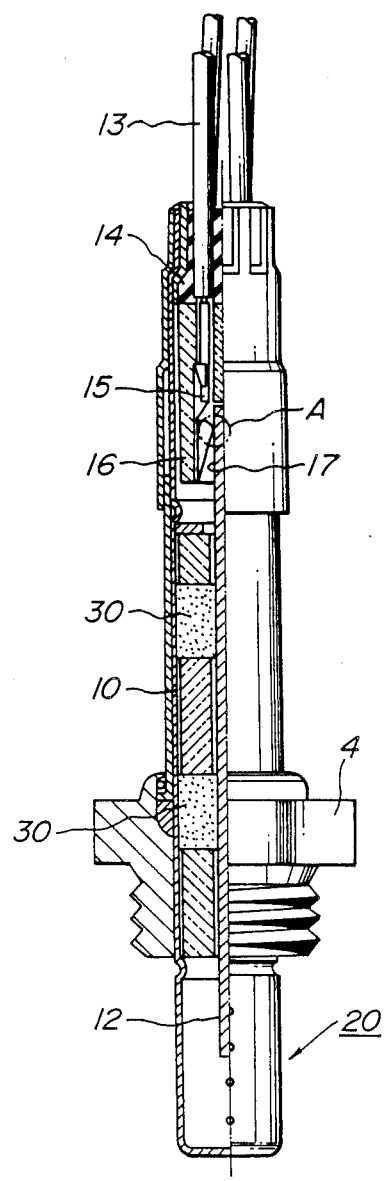
FIG_2b
PRIOR ART
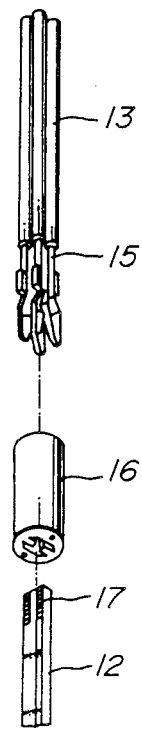

OXYGEN SENSOR

BACKGROUND OF THE INVENTION

1. Field of the Invention

The present invention relates to an improvement of an oxygen sensor, comprising electrodes, a sensor element which generates an electromotive force or which changes its electric resistance value between the electrodes depending on oxygen concentration of a gas to be measured, electrode terminals arranged on the sensor element and connected to the electrodes, and a metallic accommodating member accommodating the sensor element.

2. Related Art Statement

Heretofore, the above type of oxygen sensor 20 has ceramic powder 30 filled and compressed between a metallic cap 10 and a sensor element 12, and the compressed ceramic powder 30 fixes the sensor element 12 and separates air from the gas to be measured, if air is used as a standard oxygen atmosphere for the sensor element 12, as shown in partial crosssection in attached FIG. 2a.

The cap 10 has a rubber plug 14 at its upper open end portion opposite to a housing 4 for receiving lead wires 13 therethrough. The plug 14 is fixed at the position by caulking the cap 10 to seal the cap 10. Female contacts 15 are arranged at the end of the lead wires 13 for electrically connecting an electrode terminal 17 of the sensor element 12 and the female contacts 15 in a ceramic housing 16.

Namely, as shown as exploded perspective view in FIG. 2b, the female contact 15 per se has a resilient function and is accommodated in the ceramic housing 16, so that the female contact 15 and the ceramic housing 16 are made integral with each other to form an integral body, and the sensor element 12 is inserted in the integral body to attain electrical connection of the female contact 15 and the electrode terminal 17 of the sensor element 12 by means of the resilient function of the female contact 15 per se.

However, this type of oxygen sensor 20 has a drawback in that a high compressing pressure cannot be obtained, so that electrical connection between the electrode terminal 17 and the female contact 15 becomes unstable, because the electrode terminal 17 and the female contact 15 are contacted by means of the resilient function of the female contact 15 per se.

The oxygen sensor 20 has also a drawback in that, when inserting the sensor element 12 in the integral body, the plating layer provided on the female contact 15 at which the electrode terminal 17 of the sensor element 12 contacts, is rubbed against the end portion and the electrode terminal 17 of the sensor element 12 and peeled off therefrom at the portion A shown in FIG. 2. As a result, a drawback arises also in that the electrical connection between the female contact 15 and the electrode terminal 17 becomes bad by fretting corrosion etc., due to vibration and/or humid atmosphere during a long period of use of the oxygen sensor.

SUMMARY OF THE INVENTION

An object of the present invention is to obviate the above drawbacks.

Another object of the present invention is to provide an oxygen sensor which assures good electrical connection between the female contact and the electrode terminal during a long period of use.

To fulfill the above objects, the present invention provides an oxygen sensor, comprising electrodes, a sensor element which generates an electromotive force or which changes its electric resistance value between the electrodes depending on oxygen concentration of a gas to be measured, electrode terminals arranged on the sensor element and connected to the electrodes, and a metallic accommodating member accommodating the sensor element, comprising; a female contact electrically connected to the electrode terminal; a ceramic housing electrically insulating the female contact from the metallic accommodating member; a resilient member pressing the ceramic housing; and a caulking ring pressing the resilient member to exhibit its resilient power; the female contact, the ceramic housing, the resilient member and the caulking ring forming a consent device receiving the electrode terminal; the caulking ring being caulked to press the resilient member such that the female contact is pressed and electrically connected to the electrode terminal portion by a given pressure.

By this arrangement, the female contact can be pressed to the electrode terminal with a large resilient power by means of the resilient member and the caulking ring, so that the female contact can be assuredly connected electrically to the electrode terminal. Therefore, the oxygen sensor of the present invention does not suffer from electrical connection deficiency, such as fretting corrosion, etc., even when it is used for a long period and exposed to vibration and/or humid atmosphere, so that good electrical connection can be achieved for a long period of use.

If a protrusion is provided on the female contact for opening the contacting portions of the female contact which contact with the electrode terminal, the protrusions are contacted with the end portion and the electrode terminal of the sensor element, while the end portion and the electrode terminal of the sensor element are not contacted with the contacting portion, so that a plating layer consisting of, for example, a noble metal is advantageously not peeled off, if the contacting portion has such plating layer. The plating noble metal layer is preferably made of Au, Ag or Pt.

Brief Description of the Drawings

For a better understanding of the present invention, reference is made to the accompanying drawings, in which:

FIG. 1a is a partial crosssection view of an example of the present oxygen sensor;

FIG. 1b is an exploded perspective view of an example of a structure of electrical connection of the present oxygen sensor;

FIG. 2a is a partial crosssectional view of an example of a prior oxygen sensor; and FIG. 2b is an exploded perspective view of an example of a structure of electrical connection of a prior oxygen sensor.

Throughout different views of the drawings, 4 is a housing, 10 is a metallic cap, 12 is a sensor element, 13 is lead wires, 14 is a rubber plug, 15 is female contacts, 16 is a ceramic housing, 17 is an electrode terminal, 20 is an oxygen sensor, 22 is a sensor element, 26 is an inner cylinder, 32 is an outer cylinder, 35 is a consent, 41 is a female contact, 42 is a ceramic housing, 43 is a metallic fitting, 44 is a pressing spring, 45 is a caulking ring, 46 is an electrode terminal portion, 47 is a protrusion of the female contact 41, and 48 is a plating layer on the contacting portion of the female contact 41.

Description of the Preferred Embodiments

Hereinafter, the present invention will be explained in detail with reference to Examples.

Referring to FIGS. 1a and 1b, the oxygen sensor 20 of the present invention has a plate-shaped sensor element 22 which is surrounded by a metallic housing 24 and a metallic inner cylinder 26 firmly welded to the metallic housing 24. The sensor element 22 is fixed by means of talc 30 filled between ceramic supporters 28a, 28b and 28c, and gastightly sealed by the talc 30.

In this embodiment, in order to electrically connect the sensor element to the exterior, an electrode terminal 46 is inserted in a consent device 35 consisting of a female contact 41 connected to lead wires 36, a ceramic housing 42 divided into two sections, a metallic fitting 43, a resilient member 44 and a caulking ring 45, and then the outer circumferential periphery of the caulking ring 45 is caulked to exert a displacement to the resilient member 44 so as to press the female contact 41 against the electrode terminal 46 with a given pressure, as shown in exploded perspective view in FIG. 1b. In this embodiment, desired protrusions 47 are provided on the end portions of the female contact 41, and a plating layer 48 made of Au is provided at the contacting portion of the female contact 41 which may contact with the electrode terminal.

In the oxygen sensor of the above structure, a pressing power per one piece of the female contact 41 exerted by the resilient member 44, is preferably at least 300 times, more preferably at least 1000 times, of the total weight of the consent device 35.

In case when inserting the electrode terminal 46 in the consent device 35, the protrusions 47 of the female contact 41 assist to open the contacting portions of the female contact 41 which may contact with the electrode terminal 46, so that the noble metal plating layer 48 provided on the contacting portions of the female contact 41 which may contact with the electrode terminal 46 is not abraded at the time of inserting the electrode terminal 46 in the consent device 35, hence the peeling off of the plating layer 48 from the female contact 41 is prevented.

If the caulking ring 45 is caulked to exert the resilient member 44 to press the female contact 41 to the electrode terminal 46, the protrusions of the female contact 41 are crushed flat, so that electrical connection between the female contact 41 and the electrode terminal 46 can be attained.

In this embodiment, in order to protect the sensor element 22 from the exterior environment, a metallic outer cylinder 32 is fitted to the outer circumferential portion of an upper circular projection 34 of the metallic housing 24, and the lower end of the metallic outer cylinder 32 is welded and gastightly fixed to the outer circumferential portion of the upper circular projection 34 of the metallic housing 24 over the entire circumference of the lower end of the metallic outer cylinder 32.

Meanwhile, the upper open end of the metallic outer cylinder 32 remote from the lower end thereof welded to the housing 24, receives a rubber plug having lead wires 36 therein, and caulked to fix the rubber plug 38, so as to seal the outer cylinder 32.

By preventing the peeling off of the plating layer at the surface of the contacting portion of the female contact 41 which may contact with the electrode terminal 46 of the sensor element 22 and by enhancing the pressing power of the contacting portion of the female contact 41 to the electrode terminal 46 in this way, the drawbacks of electrical connection deficiencies, such as fretting corrosion, etc., can be eliminated, even when the oxygen sensor is exposed to vibrations and/or humid atmosphere for a long period of use.

As apparent from the foregoing explanations, the oxygen sensor of the present invention uses a consent device constituted such that the electrical connection between the female contact and the electrode terminal of the sensor element is achieved by external pressing power of the resilient member, so that a large pressing power can be exerted on the female contact to achieve an ensured electrical connection between the female contact and the electrode terminal. Therefore, superior electrical connection between the female contact and the electrode terminal of the sensor element can be attained for a long period without causing an electrical connection deficiency, even when the oxygen sensor is exposed to vibrations and/or humid atmosphere for a long period of use.

Although the present invention has been explained with specific embodiments, it is of course apparent to those skilled in the art that various changes and modifications are possible without departing from the broad spirit and aspect of the present invention as defined in the appended claims.

What is claimed is:

1. An oxygen sensor, comprising electrodes a sensor element which generates an electromotive force or which changes its electric resistance value between the electrodes depending on the oxygen concentration of the gas to be measured, electrode terminals arranged on the sensor element and connected to the electrodes, and a metallic accommodating member accommodating the sensor element, comprising; a female contact electrically connected to the electrode terminal; a ceramic housing electrically insulating the female contact from the metallic accommodating member; a resilient member pressing the ceramic housing; and a caulking ring pressing the resilient member to exhibit its resilient power; the female contact, the ceramic housing, the resilient member and the caulking ring forming a consent device receiving the electrode terminal; the caulking ring being caulked to press the resilient member such that the female contact is pressed and electrically connected to the electrode terminal by a given pressure.

2. The oxygen sensor as defined in claim 1, comprising a protrusion provided on the female contact for opening the contacting portions of the female contact which may contact with the electrode terminal.

* * * * *